(12) United States Patent
Nakabayashi et al.

(10) Patent No.: US 10,640,886 B2
(45) Date of Patent: May 5, 2020

(54) FIBER-CONTAINING CRYSTAL, METHOD OF PREPARING FIBER-CONTAINING CRYSTAL, APPARATUS FOR PREPARING FIBER-CONTAINING CRYSTAL, AND MEDICINE SOAKING APPARATUS

(71) Applicant: Toray Industries, Inc., Tokyo (JP)

(72) Inventors: Iori Nakabayashi, Otsu (JP); Hiroshi Tsuchikura, Otsu (JP); Atsushi Kuwabara, Otsu (JP); Hiroaki Adachi, Minoh (JP)

(73) Assignee: Toray Industries, Inc., Tokyo (JP)

( * ) Notice: Subject to any disclaimer, the term of this patent is extended or adjusted under 35 U.S.C. 154(b) by 113 days.

(21) Appl. No.: 15/766,955

(22) PCT Filed: Sep. 28, 2016

(86) PCT No.: PCT/JP2016/078588
§ 371 (c)(1),
(2) Date: Apr. 9, 2018

(87) PCT Pub. No.: WO2017/061314
PCT Pub. Date: Apr. 13, 2017

(65) Prior Publication Data
US 2019/0177877 A1  Jun. 13, 2019

(30) Foreign Application Priority Data
Oct. 9, 2015 (JP) .................................. 2015-201575

(51) Int. Cl.
*C30B 29/58* (2006.01)
*C30B 7/00* (2006.01)
*C07K 1/30* (2006.01)
*C12N 15/09* (2006.01)

(52) U.S. Cl.
CPC .............. *C30B 29/58* (2013.01); *C07K 1/306* (2013.01); *C30B 7/00* (2013.01); *C12N 15/09* (2013.01)

(58) Field of Classification Search
CPC ............ C30B 29/58; C12N 15/09; C07K 1/14
See application file for complete search history.

(56) References Cited

U.S. PATENT DOCUMENTS

| 2005/0075482 A1 | 4/2005 | Tanaka et al. |
| 2013/0172478 A1* | 7/2013 | Bausch .................... C07K 7/06 524/555 |

FOREIGN PATENT DOCUMENTS

| JP | 2007-254415 A | 10/2007 |
| WO | 03/053998 A1 | 7/2003 |
| WO | 2009/091053 A1 | 7/2009 |

OTHER PUBLICATIONS

Jose A. Gavira et al., "Growth of Ultrastable Protein-Silica Composite Crystals," *Crystal Growth & Design*, vol. 13, No. 6, Jun. 5, 2013. pp. 2522-2529.

(Continued)

*Primary Examiner* — Robert M Kunemund
(74) *Attorney, Agent, or Firm* — DLA Piper LLP (US)

(57) ABSTRACT

A fiber-containing crystal includes a crystal body which is a crystal of a biological substance and a plurality of fibers at least partially incorporated in the crystal body; and a fiber-containing crystal includes a crystal body which is an easy-disintegrating crystal and a plurality of fibers at least partially incorporated in the crystal body.

12 Claims, 6 Drawing Sheets

(56) References Cited

OTHER PUBLICATIONS

Miki Matsuoka et al., "Growth of high-strength protein crystals with nanofibers," *Applied Physics Express*, vol. 9, No. 3, Feb. 9, 2016, pp. 035503-1-035503-3.
Extended European Search Report dated May 17, 2019, of counterpart European Application No. 16853468.3.
Shigeru Sugiyama et al., "Growth of Protein Crystals in Hydrogels Prevents Osmotic Shock," Journal of the American Chemical Society, vol. 134, 2012, pp. 5786-5789.
Miki Matsuoka et al., "Protein crystallization with paper," Japanese Journal of Applied Physics, vol. 55, Apr. 12, 2016, pp. 050302-1-050302-3.
Notice of Reasons for Refusal dated Sep. 24, 2019, of counterpart Japanese Application No. 2015-201575, along with an English translation.

* cited by examiner

| | Solution | Example 2 (Dropping amount: 0.5 µL) | Example 3 (Dropping amount: 1.0 µL) | Example 4 (Dropping amount: 1.5 µL) | Example 5 (Dropping amount: 2.0 µL) |
|---|---|---|---|---|---|
| Immediately after the beginning of immersion | | | | | |
| 20 seconds later | | | | | |
| 40 seconds later | | | | | |
| 60 seconds later | | | | | |
| 80 seconds later | | | --- | | --- |
| 100 seconds later | | | --- | | --- |
| 120 seconds later | | --- | --- | --- | --- |

FIG. 11

FIBER-CONTAINING CRYSTAL, METHOD OF PREPARING FIBER-CONTAINING CRYSTAL, APPARATUS FOR PREPARING FIBER-CONTAINING CRYSTAL, AND MEDICINE SOAKING APPARATUS

TECHNICAL FIELD

This disclosure relates to a fiber-containing crystal, a method of preparing the fiber-containing crystal, an apparatus for preparing the fiber-containing crystal, and a chemical soaking apparatus. More particularly, the disclosure relates to a fiber-containing crystal which is excellent in mechanical strength and allows implementation of highly accurate structure analysis, a method of preparing such fiber-containing crystal, an apparatus for preparing such fiber-containing crystal, and a chemical soaking apparatus using such fiber-containing crystal.

BACKGROUND

Conventionally, three-dimensional structure analysis of biological substances such as proteins and nucleic acids has been promoted. To elucidate a three-dimensional structure of a biological substance is crucial in developing, for example, a new medicine or the like that can combine with the biological substance. As a technique of analyzing the three-dimensional structure of biological substances, for example, crystal structure analysis is known. Crystal structure analysis is a technique to determine the structure of a crystal, in which a crystal of a biological substance is prepared, diffraction of X-rays or the like by the crystal lattice is performed, and result of the diffraction is analyzed.

Unfortunately, the crystals of biological substances are extremely brittle unlike the crystals of inorganic compounds, and they are thus difficult to handle. To solve this problem, a technique for crystallizing a biological substance in a gel has been proposed (WO 2009/091053).

The crystal preparing method described in WO '053 is useful in that it can easily prepare a crystal compared to a method of precipitating a crystal from a solution. However, the gel is easily dried, and that needs to be taken care of. Also, the work to take out the crystal formed in the gel requires some skills. Therefore, there is room for further improvement in the method described in WO '053.

It could therefore be helpful to provide a fiber-containing crystal excellent in mechanical strength, easy to handle, and allows for highly accurate structure analysis, and a method of preparing such fiber-containing crystal; an apparatus for preparing the fiber-containing crystal; and a chemical soaking device using such fiber-containing crystal.

SUMMARY

We found that, by incorporating a plurality of fibers, the crystal to be obtained becomes excellent in mechanical strength, easy to handle, and allows for highly accurate structure analysis, and thus they completed the disclosure.

We thus provide:

A fiber-containing crystal comprising a crystal body which is a crystal of a biological substance and a plurality of fibers which are at least partially incorporated in the crystal body.

A method of preparing a fiber-containing crystal, comprising a preparation step for preparing a plurality of fibers; an addition step for adding a solution in which a biological substance is dissolved to the plurality of fibers; a crystallization step for precipitating a crystal by increasing the concentration of the biological substance in the solution; and an extraction step for extracting, out of the obtained crystals, a fiber-containing crystal incorporating a part of a plurality of fibers inside.

An apparatus for preparing the fiber-containing crystal, comprising a fiber holding part on which a plurality of fibers are laid; a solution holding part holding a solution in which a biological substance is dissolved; a solution addition part extracting the solution from the solution holding part and adding the solution onto the plurality of fibers laid on the fiber holding part; and an extraction part extracting, out of the crystals precipitated in the solution after a predetermined period of time, a fiber-containing crystal incorporating at least a part of the plurality of fibers inside.

A chemical soaking device comprising a crystal holding part holding a fiber-containing crystal, wherein the fiber-containing crystal contains a crystal body which is a crystal of a biological substance and a plurality of fibers at least partially incorporated in the crystal body; a chemical holding part holding a chemical solution in which a chemical is dissolved; and a chemical addition part extracting the chemical from the chemical holding part and adding the chemical to the fiber-containing crystal.

DETAILED DESCRIPTION

Fiber-Containing Crystal

A fiber-containing crystal comprises a crystal body and a plurality of fibers partially incorporated in the crystal body. The following describes constitutions thereof respectively.

Crystal Body

The crystal body is either a crystal of a biological substance or an easy-disintegrating crystal. In the following explanation, a description common to both of a crystal of a biological substance and an easy-disintegrating crystal may collectively refer them as a crystal of "a biological substance or the like."

The biological substance is a main component of the fiber-containing crystal. The biological substance is not particularly limited. Examples of the biological substance include a biopolymer, a protein, a peptide, a nucleic acid, a sugar chain, a glycolipid, a glycoprotein, a vector, an antibody, an antigen, or the like.

The term "biological substance" may be a substance derived from an organism, a synthetic substance having the same structure, or a derivative or artificial substance having a similar structure. Specifically, for example, when the biological substance is a biopolymer, the biopolymer may be a macromolecule derived from a living organism, a synthetic macromolecule having the same structure, or a derivative or artificial macromolecule having a similar structure. Also, when the biological substance is a protein, the protein may be a protein derived from a living organism (a naturally occurring protein) (a native protein), a synthetic protein, or an artificial protein not occurring naturally. When the biological substance is a peptide, the peptide may be a peptide derived from a living organism (a naturally occurring peptide) (a native peptide), a synthetic peptide, or an artificial peptide not occurring naturally. When the biological substance is a nucleic acid, the nucleic acid may be a nucleic acid derived from a living organism (a naturally occurring nucleic acid) (a native nucleic acid), a synthetic nucleic acid, or an artificial nucleic acid not occurring naturally. When the biological substance is a sugar chain, the sugar chain may be a sugar chain derived from a living organism (a naturally occurring sugar chain) (a native sugar chain), a synthetic sugar chain, or an artificial sugar chain not occurring naturally.

The fiber-containing crystal, as described below, may have a mechanical strength enhanced by a plurality of fibers incorporated therein. Thus, even though the biological substance is a substance that naturally forms a brittle crystal such as a biopolymer, a protein, a peptide, a nucleic acid and a sugar chain, it can form a fiber-containing crystal which has sufficiently enhanced mechanical strength. Consequently, highly accurate analysis of these biological substances is possible.

The molecular weight of the biological substance is not particularly limited. In other words, the molecular weight of the biological substance depends on its type. For example, when the biological substance is a biopolymer, the molecular weight thereof is, for example, 5000 or more. Also, when the biological substance is a peptide, the molecular weight thereof is, for example, 1000 or more.

The easy-disintegrating crystal is a crystal comprising an easy-disintegrating substance. The easy-disintegrating substance is a main component of the fiber-containing crystal. The easy-disintegrating crystal refers to a crystal having a crystalline form easily disintegrated by physical stress or by contact with chemical substances such as a solvent. Examples of the easy-disintegrating crystal include crystals having a relatively large gap in the crystal body and formed by a relatively weak bonding such as a protein, a peptide, a nucleic acid, and a sugar chain. Further, the easy-disintegrating crystal is not limited to those biological substances, and any crystal having the same form as mentioned above is also referred to as easy-disintegrating crystal. The following description mainly explains a typical biological substance which forms an easy-disintegrating crystal. The easy-disintegrating crystal is not particularly limited to a crystal of the biological substance, and it also includes other easy-disintegrating crystal bodies. Specifically, the crystal of easy-disintegrating substance is a crystal having a Vickers hardness of 10 HV or lower, measured by "JIS Z 2244: 2009 Vickers hardness test," more preferably a crystal having a Vickers hardness of 5 HV or lower. The lower limit of the Vickers hardness is not particularly specified. It may have an Vickers hardness unmeasurable with the measuring equipment used in the above test method. For example, an ultra-macromolecule of a self-organizing organic compound is difficult to be crystallized and, even if a crystal is formed, it could be easy-disintegrable and may be usefully employed. The crystal body, which is an easy-disintegrating crystal as described, may have a mechanical strength enhanced by a plurality of fibers incorporated therein, as described below. Specifically, its Vickers hardness may be increased to 0.05 HV or higher, more preferably 0.1 HV or higher. Therefore, even though the crystal body comprises an easy-disintegrating substance, it can form a fiber-containing crystal having a sufficiently enhanced mechanical strength. Consequently, highly accurate analysis of these easy-disintegrating substances is possible.

Returning to the description of the whole crystal body, the size of the crystal body is not particularly limited. The size of the crystal body may be determined according to the purpose of use. For x-ray structure analysis, the fiber-containing crystal has preferably a size of 5-μm cube or more and, with an x-ray free-electron laser, that allows structure analysis of a nano-sized crystal, the lower limit value of the size may be 50-nm cube or more. The upper limit is also not particularly specified, and the crystal body may be grown to a desired size. For neutron beam diffraction, relatively large crystal is desirable, it is satisfactory if the fiber-containing crystal has about a size of 10-mm cube. In the above, expressions such as "5-μm cube or more" are not intended to limit the shape, but the fiber-containing crystal is expected to have about the size mentioned.

Fiber

The fiber is a fiber partially incorporated in the crystal body. In the fiber-containing crystal, a plurality of fibers are incorporated in the crystal body. The fiber may be fully incorporated in the interior of the crystal body, or may be partially incorporated so that a part thereof is exposed to the outside from the surface of the crystal body. In the fiber-containing crystal, at least a plurality of fibers are incorporated, being exposed from the surface of the crystal body.

The type of the fiber is not particularly limited. As an example, a polyolefin-based fiber such as polyethylene, a nylon-based fiber, a polyester-based fiber, an acryl-based fiber, an aramid (wholly aromatic polyamide) fiber, a cellulose-based fiber, a polyarylate (wholly aromatic polyester) fiber, or the like can be used as the fiber. More specifically, the fiber is an aramid fiber (meta-aramid fiber, para-aramid fiber), a polytetrafluoroethylene fiber, a cellulose-based fiber, a polyarylate (wholly aromatic polyester) fiber, or the like. Among these, the fiber is preferably an aramid fiber, a cellulose-based fiber, or a polyarylate fiber because they are easily fine-processed and easily incorporated in the crystal body, and are excellent in mechanical properties such as strength and elasticity.

The length of the fiber is not particularly limited. The length depends on whether the fiber is present in a straight shape or in a curved shape and on the size of the crystal to be grown to. When the fiber is too long, the part exposed from the surface of the crystal body tends to entangle with a fiber which is not incorporated, making the extraction difficult. The length of the fiber thus may be selected according to the size of the crystal. For example, the length of the fiber is preferably 100 nm or more, more preferably 1 µm or more. Also, the length of the fiber is preferably 10 mm or less, more preferably 1 mm or less, further preferably about one-tenth of the crystal size to be obtained or less. If many of the contained fibers are 100 nm to 1 mm in length and shorter than one-tenth of the crystal size to be obtained, the part exposed from the surface of the crystal body does not become too long in crystallization, and the crystal to be obtained is excellent in handling property.

The thickness (diameter) of the fiber is not particularly limited. For example, the thickness of the fiber is preferably 1 nm or more, more preferably 10 nm or more. Also, the thickness of the fiber is preferably 100 µm or less, more preferably 10 µm or less. When it has a thickness of 10 nm to 10 µm, the fiber is, in crystallization, likely to be incorporated with at least a part thereof exposed from the surface of the crystal body. Also, such fiber is likely to increase the mechanical strength of the crystal body. The fiber may be in a shape of a single line or may be in a shape of a multiply branched pulp in which a single thick fiber fibrillated.

Also, the thickness (diameter) of the fiber may be defined based on the relationship with the size of the entire crystal, instead of the actual size described above or in accordance with the actual size. Specifically, the thickness (diameter) of the fiber is preferably 1/1000 of the diameter of the crystal or more, more preferably 1/500 or more. Also, the thickness (diameter) of the fiber is preferably 1/10 of the diameter of the crystal or less, more preferably 1/20 or less. When the thickness (diameter) of the fiber is within the above range, the fiber is likely to be partially incorporated in the crystal body. Thus, the crystal to be obtained is more easy to handle, and highly accurate structure analysis is easy to perform.

The form of the fiber is not particularly limited as long as incorporation of a plurality of fibers in the crystal is possible. The fiber may form a web in which the fiber is curled in a certain shape (such as helical or wavy shape) to be curved, or a plurality of fibers cross each other or are entangled with each other; a spiral shape; or other three-dimensional networks such as a woven knitted fabric. When a fiber forming such network is incorporated at least partially in the crystal body, the crystal body can be protected from a small external force applied by a solution flowing around the crystal body and a load at the time of extracting the fiber-containing crystal. Consequently, the fiber-containing crystals are less likely to be broken. The expression "a plurality of fibers" in "a plurality of fibers which are at least partially incorporated in the crystal body" means that a plurality of fibers are incorporated in the crystal body, which includes when a fiber projected from the crystal body forms a loop and is contained again in the crystal body. More specifically, the fiber may be in a pulp-like form or in a form of an aggregate, a nonwoven fabric, a woven fabric or the like of a fiber (preferably a nanofiber defined as a fiber having a fiber diameter of 1 µm or less).

The fiber may be a fiber commercially available or may be prepared. Examples of a preerable fiber include aramid fiber pulp such as meta aramid fiber pulp and para aramid fiber pulp, polyarylate fiber pulp, polytetrafluoroethylene fiber pulp, cellulose fiber pulp, kraft pulp, waste paper pulp, and mechanical pulp. More preferably, the fiber is aramid fiber pulp, cellulose-based fiber pulp, or polyarylate fiber pulp. Commercial products such as Kevlar (registered trademark) pulp, manufactured by Du Pont-Toray Co., Ltd., and Twaron (registered trademark) pulp, manufactured by Teijin Aramid BV are appropriately used as the fiber. When the fiber is to be prepared, the preparation method is not particularly limited. For example, the fiber is prepared by beating or fine-shredding a short-cut fiber, woven fabric, or nonwoven fabric. Specifically, the fiber is, after being appropriately beaten or fine-shredded, suspended in a solvent such as ethanol, and then centrifugally-separated. The obtained supernatant contains fibers shorter in length and smaller in diameter. This supernatant is collected and dried as necessary. Thus, fibers adjusted to have a length and thickness within the above ranges can be prepared.

Figure 1:
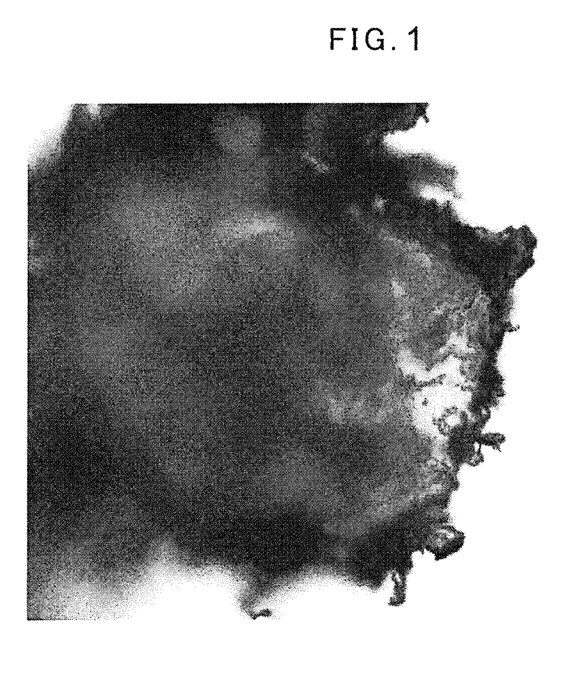
FIG. 1 is a photomicrograph of a fiber-containing crystal.

Returning to the description of the entire fiber-containing crystal, FIG. 1 is a photomicrograph of a fiber-containing crystal. FIG. 1 illustrates a fiber-containing crystal in which a plurality of meta-aramid pulps are incorporated in a crystal body of lysozyme. As shown in FIG. 1, in the fiber-containing crystal, a plurality of fibers incorporated therein are partially exposed to the outside from the surface of the crystal body. The fiber is small in thickness and thus flexible. Thus, the fiber of the fiber-containing crystal can be in point contact with a surface on which the crystal is precipitated (a precipitation surface). Such fiber-containing crystal, being in point contact with the precipitation surface, can be extracted by scooping up the exposed fiber portion without touching the crystal body itself. Alternatively, the fiber-containing crystal grows while incorporating a plurality of fibers, wherein the crystal is formed on and in contact with residual fibers which are not contained in the crystal (fibers not contained in the fiber-containing crystal and in contact with the crystal). Such fiber-containing crystal, being in point contact with the precipitation surface, can be easily extracted by scooping up the exposed fiber portion. Consequently, compared to when the crystal itself is in surface contact with the precipitation surface, the fiber-containing crystal is easily extracted from the precipitation surface. Therefore, the fiber-containing crystal to be obtained is less likely to be broken.

As shown in FIG. 1, a plurality of fibers exposed from the periphery of the crystal body forms a three-dimensional network (or a web) in which each fiber is curled in a certain shape (such as helical or wavy shape) to be curved or the plurality of fibers cross each other or are entangled with each other. When the fiber-containing crystal body contains at least a part of such network in the crystal, the interior of the crystal body is reinforced by the plurality of fibers. Therefore, the crystal body can be protected from a small external force applied by a solution flowing around the crystal body and a load at the time of extracting the fiber-containing crystal. Consequently, the fiber-containing crystal is less likely to be broken.

Further, as shown in FIG. 1, a plurality of fibers are incorporated in the crystal body in irregular directions respectively. Therefore, these fibers are, for example, in crystal structure analysis, less likely to be recognized as a diffraction point and hardly affect a structure analysis result. Consequently, highly accurate structure analysis of the fiber-containing crystal is possible.

The technique of analyzing the structure of the fiber-containing crystal is not particularly limited. For example, the structure of the fiber-containing crystal can be analyzed by a technique such as x-ray crystal structure analysis, neutron crystal structure analysis, and electron microscope observation. In any of these structure analysis methods, the fiber-containing crystal, which has a mechanical strength enhanced by incorporating a plurality of fibers, is less likely to be broken, and a highly reliable analysis data is likely to be obtained.

Method of Preparing Fiber-Containing Crystal

A method of preparing a fiber-containing crystal is a method of preparing a fiber-containing crystal, comprising a preparation step of preparing a plurality of fibers; an addition step of adding a solution in which a biological substance or the like is dissolved to the plurality of fibers; a crystallization step of precipitating a crystal by increasing the concentration of the biological substance or the like in the solution; and an extraction step of extracting out of the obtained crystals a fiber-containing crystal incorporating at least a part of a plurality of fibers inside. The following describes constitutions thereof respectively.

Preparation Step

In the preparation step, a plurality of fibers are prepared. The fiber is the same as those described above in the fiber-containing crystal. According to the preparation step, a plurality of fibers are laid in a plate. The shape of the plate is not particularly limited. The plate is preferably a flat, bottomed cylindrical plate (e.g., a petri dish), which allows easy addition of a solution in an addition process described below.

In the preparation step, the fiber is used in this manner. Thus, a problem such as drying of gel does not occur unlike, for example, the conventional way using gel. In terms of handling property, it is preferable that a liquid containing the fiber is, for example, dropped onto the plate for addition to the plate and dried on the plate. Also, the plate used in the method of preparing the fiber-containing crystal in which the fiber laid thereon is dried, is excellent in handling properties in storage and distribution. Drying the fibers can be performed, for example, by drying them at 80° C. for 12 hours or more with a dryer.

Addition step

In the addition step, a solution in which a biological substance or the like is dissolved is added onto a plurality of fibers. The biological substance or the like is the same as those described above the fiber-containing crystal. The biological substance or the like has been dissolved in an appropriate solvent in advance so that the solution has a predetermined concentration. This solution is added onto the fiber laid on the plate. The method of addition is not particularly limited. For example, a method in which the solution is sucked with a suction device (e.g., a pipette device with a suction tip attached thereto) and then added onto the fiber by being dropped thereon may be adopted.

The addition step thus can be performed by a simple operation of dropping a solution in which a biological substance or the like is dissolved on the fiber. Therefore, the addition process does not require skills in work and is highly reproducible.

The solvent comprised in the solution is not particularly limited. For example, solvents used in known crystal preparing methods may be used. More specifically, examples of the solvent include water, ethanol, methanol, acetonitrile, acetone, anisole, isopropanol, ethyl acetate, butyl acetate, chloroform, cyclohexane, diethylamine, dimethylacetamide, dimethylformamide, toluene, butanol, butyl methyl ether, hexane, benzene, methyl ethyl ketone and the like.

The concentration of the biological substance or the like in the solution is not particularly limited. For example, the concentration of the biological substance or the like is preferably 0.2 mg/mL or more, more preferably 0.5 mg/mL or more, further preferably 1.0 mg/mL or more. Also, the concentration of the biological substance or the like is preferably 300 mg/mL or less, more preferably 100 mg/mL or less, further preferably 50 mg/mL or less. When the concentration of the biological substance or the like is within the above-mentioned range, the preparation is relatively easy, and a crystal is easily precipitated in a crystallization process described below. A pH adjuster or the like may be appropriately mixed to the solvent.

Crystallization Step

In the crystallization step, a crystal is precipitated by increasing the concentration of the biological substance or the like in the solution. A method for the crystallization is not particularly limited. The crystallization may be performed by simply leaving the solution and waiting for a crystal of the biological substance to be precipitated. Also, a precipitating agent solution may be added to the solution. The precipitating agent is not particularly limited. For example, precipitation agents used in known crystal preparing methods may be used. More specifically, the precipitating agent can be sodium chloride, calcium chloride, sodium acetate, ammonium acetate, ammonium phosphate, ammonium sulfate, potassium sodium tartrate, sodium citrate, polyethylene glycol (PEG), magnesium chloride, sodium cacodylate, 2-[4-(2-hydroxyethyl))-1-piperazinyl] ethanesulfonic acid (HEPES), 2-methyl-2,4-pentanediol (MPD), tris(hydroxymethyl)aminomethane (Tris-HCl), or the like. The solvent in the precipitating agent solution is not particularly limited. The solvent in the precipitating agent solution may be the same as that in the solution of the biological substance or the like as mentioned above. The concentration of the precipitating agent is not particularly limited. For example, the concentration of the precipitating agent is preferably 0.0001 M or more, more preferably 0.0005 M or more. Also, the concentration of the precipitating agent is preferably 10 M or less, more preferably 8 M or less, further preferably 6 M or less. When the concentration of the precipitating agent is within the above range, a crystal of the biological substance tends to be produced. A pH adjusting agent or the like may be appropriately mixed to the precipitating agent.

Extraction Step

In the extraction step, a fiber-containing crystal incorporating at least a part of a plurality of fibers is extracted out of the obtained crystals. In the extraction step, for example, an observation device (such as an optical microscope) is used to observe the inside of the plate to select a desired fiber-containing crystal, and then extraction thereof is performed.

The fiber-containing crystal may be selected visually by an observer or may be automatically selected by a computer or the like executing a program in which the shape of the crystal or the like is stored in advance. The selected fiber-containing crystal may be extracted by the suction device described in the above addition step or may be extracted together with the surrounding solution by a loop-shaped, mounting device (a cryoloop).

As described above, a part of the plurality of fibers incorporated in the fiber-containing crystal is exposed to the outside from the surface of the crystal body. The fiber is small in thickness and thus flexible. Thus, the fibers of the fiber-containing crystal can be in point contact with a surface on which the crystal is precipitated (a precipitation surface). When, for example, a loop-shaped mounting device is used for the extraction, such fiber-containing crystal, being in point contact with the precipitation surface, can be extracted by scooping up the exposed fiber portion such that the mounting device itself does not touch the crystal body itself. Consequently, compared to when the crystal itself is in surface contact with the precipitation surface, the fiber-containing crystal is easily extracted from the precipitation surface. Therefore, the obtained fiber-containing crystal is less likely to be broken.

Structure analysis of the extracted fiber-containing crystal may be performed without chemical soaking or may be performed after chemical soaking. Each of them is described below. Subsequent steps when structure analysis is performed without chemical soaking Freezing Step When structure analysis is performed without chemical soaking, it is preferable that the method of preparing the fiber-containing crystal further includes a freezing step of freezing the fiber-containing crystal obtained after the extraction step. The freezing step is more preferably performed after the fiber-containing crystal is immersed in an anti-freeze agent. This prevents water in the crystal from forming ice crystals.

The anti-freeze agent is not particularly limited. Examples of the anti-freeze agent include glycerol (glycerin), 2-methyl-2,4-pentanediol (MPD), dimethyl sulfoxide (DMSO), polyethylene glycol (PEG), lithium acetate, and the like. The anti-freeze agent may be used as it is, or an aqueous solution thereof in which the anti-freeze agent is appropriately diluted with water may be used.

In a conventional method of preparing a crystal, a crystal may be damaged by an anti-freeze agent. Thus, addition of an anti-freeze agent has required fine adjustment of an amount (concentration) of the anti-freeze agent and screening of an optimum condition. Furthermore, an ideal anti-freeze agent has to be searched for according to the type of a biological substance or the like. On the contrary, the fiber-containing crystal has a strength enhanced by the fibers incorporated in the crystal body. Thus, the concentration of the anti-freeze agent is not particularly limited. For example, the crystal can be directly immersed in 100% glycerol, DMSO, PEG or the like or in a high concentration aqueous solution (e.g., 50 to 60% by mass) of glycerol, DMSO, PEG or the like. The crystal also can be immersed in a low concentration aqueous solution (e.g., 10 to 50% by mass) of glycerol, DMSO, PEG, or the like for a long period of time. More specifically, when the fiber-containing crystal is immersed in a 25% glycerol solution, for example, the crystal structure is not broken in an immersion for 120 seconds or more and even in an immersion for 300 seconds or more.

The method of freezing the fiber-containing crystal is not particularly limited. For example, the fiber-containing crystal can be frozen by a method in which the fiber-containing crystal is immersed in liquid nitrogen, a method in which nitrogen is sprayed onto the fiber-containing crystal, or the like. The temperature for freezing is not particularly limited. In general, for example, when x-ray crystal structure analysis is performed, the crystal is frozen at a temperature of 100 K or less so that water in the fiber-containing crystal is frozen in an amorphous state. Consequently, the moisture in the fiber-containing crystal hardly affects a structure analysis result.

After the freezing step, the fiber-containing crystal is then subjected to a structure analysis step described below.

Subsequent Steps When Structure Analysis is Performed After Chemical Soaking

Chemical Immersion Step

If chemical soaking is performed, it is preferable that the method of preparing the fiber-containing crystal further includes a chemical immersion step of immersing the fiber-containing crystal extracted in the extraction step into a chemical solution in which a chemical is dissolved. The chemical soaking is a method of preparing a crystal of a complex by immersing the fiber-containing crystal in a chemical solution in which a chemical is dissolved. For example, according to the chemical immersion step, a plate with a plurality of wells (recesses) formed thereon is used. In each well, each of a plurality of chemical agents of different types and concentrations are stored. The fiber-containing crystal is added to each well. Subsequently, the same method as described in the above crystallization step is performed to increase the concentrations of the biological substances or the like and the chemicals so that a complex in which the biological substance or the like comprised in the fiber-containing crystal is bonded with the chemical can be produced. The produced complex is extracted as a complex crystal by the same method as described in the above extraction step.

The bonding between the biological substance or the like and the chemical may be in any manner of bonding. For example, the bonding between the biological substance or the like and the chemical may be a covalent bond, an ionic bond, a chelate bond, a coordination bond, a hydrophobic bond, hydrogen bonding, van der Waals bonding, bonding by electrostatic force, or the like.

Freezing Step

In the freezing step, the fiber-containing crystal after the chemical immersion step is frozen. The freezing step is the same as the above-described freezing step in the case "when structure analysis is performed without chemical soaking." It is more preferable that the freezing step is carried out after the fiber-containing crystal is immersed in the anti-freeze agent. According to the freezing step, a frozen complex crystal can be obtained.

According to the method of preparing the fiber-containing crystal, the steps described above are performed to prepare the fiber-containing crystal (or a complex crystal of the fiber-containing crystal and the chemical). The mechanical strength of the obtained fiber-containing crystal is enhanced by a plurality of fibers incorporated therein. Also, the plurality of fibers can be incorporated in irregular directions respectively in the crystal body. Therefore, these fibers are, for example, in crystal structure analysis, less likely to be recognized as a diffraction point and hardly affect a structure analysis result. Consequently, highly accurate structure analysis of the fiber-containing crystal is possible.

Structure Analysis Step

Structure analysis of the fiber-containing crystal can be performed by a variety of conventional structure analysis techniques. For example, the structure analysis can be performed by a technique such as x-ray crystal structure analysis, neutron crystal structure analysis, and electron microscope observation. In any of these structure analysis techniques, the fiber-containing crystal, which has a mechanical strength enhanced by incorporating a plurality of fibers, is less likely to be broken, and a highly reliable analysis data is likely to be obtained. In the following, an example in which structure analysis of the fiber-containing crystal obtained after the above crystallization step and extraction step is performed by the technique of x-ray crystal structure analysis is illustrated.

The fiber-containing crystal extracted in the extraction step is placed on a plate and is appropriately immersed in the anti-freeze agent. Because the strength of the fiber-containing crystal is enhanced, the fiber-containing crystal does not disintegrate even though it is immersed for a long period of time (e.g., for 300 seconds in an aqueous solution of 0.2 M sodium acetate-5% NaCl-25% glycerol). Subsequently, the fiber-containing crystal is scooped up by a loop-shaped mounting device. After being scooped up, the fiber-containing crystal is, for example, immersed in liquid nitrogen so that it becomes frozen (see the freezing step as described above). The frozen fiber-containing crystal is analyzed with an x-ray crystal structure analyzer. "Disintegration" of the fiber-containing crystal caused by being immersed in the anti-freeze agent in the above description means that its structure changes to such a degree that the x-ray crystal structure analysis cannot be performed.

Specifically, the fiber-containing crystal is subjected to a monochromatic x-ray for obtaining an x-ray diffraction image (diffraction data). From the obtained diffraction data, an electron density of the biological substance or the like is obtained. Further, from the obtained electron density, a structural coordinate of the biological substance or the like is obtained. Then, based on the obtained structural coordinate, a three-dimensional structure of the biological substance or the like is analyzed. The fiber-containing crystal contains a plurality of fibers. These fibers are irregularly incorporated in the crystal body, and thus are less likely to be recognized as a diffraction point and hardly affect a structure analysis result. Consequently, a highly accurate analysis result is obtained. Also, even if they are in order and generate a diffraction point, a good structure analysis can be performed by measuring a diffraction point with only ordered fibers and removing it from a diffraction result of the fiber-containing crystal.

Figure 2:
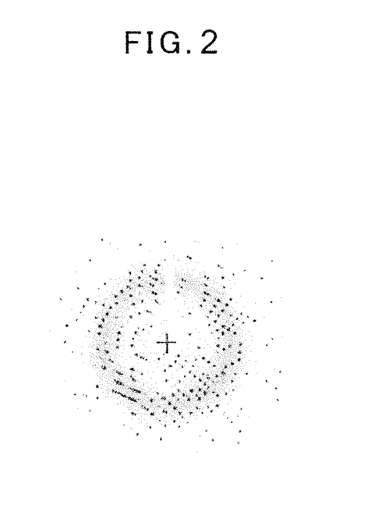
FIG. 2 is a diffraction image of a fiber-containing crystal immersed in an anti-freeze agent for 120 seconds in the freezing step.
Figure 3:
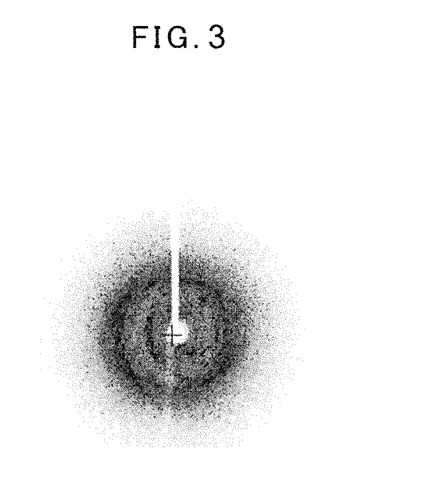
FIG. 3 is a diffraction image of a conventional crystal immersed in an anti-freeze agent for 120 seconds in the freezing step.
Figure 4:
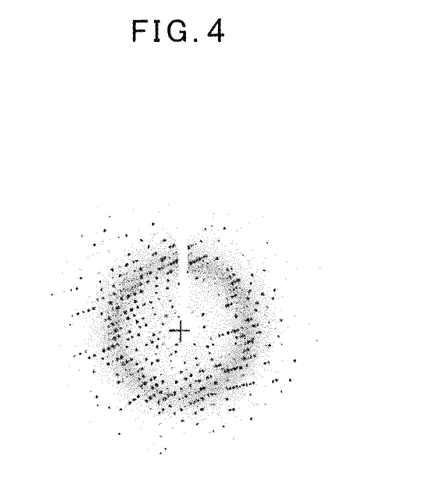
FIG. 4 is a diffraction image of a fiber-containing crystal immersed in an anti-freeze agent for 300 seconds in the freezing step.
Figure 5:
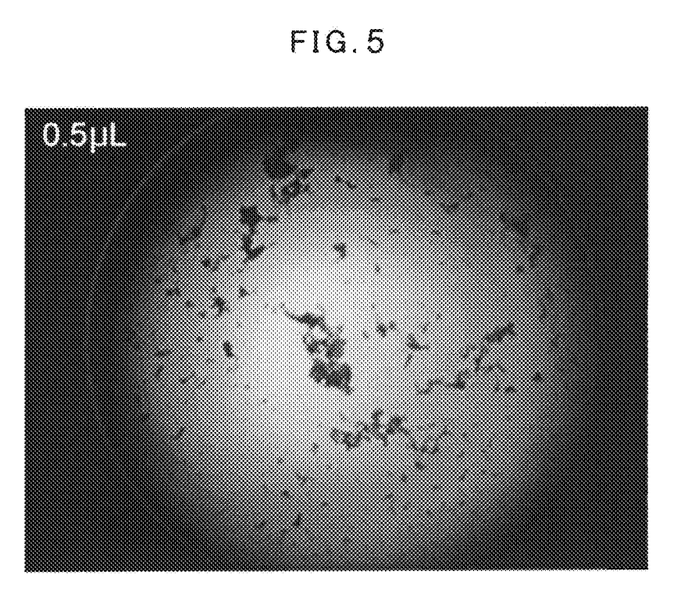
FIG. 5 is a photomicrograph of a fiber-containing crystal obtained in Example 2.
Figure 6:
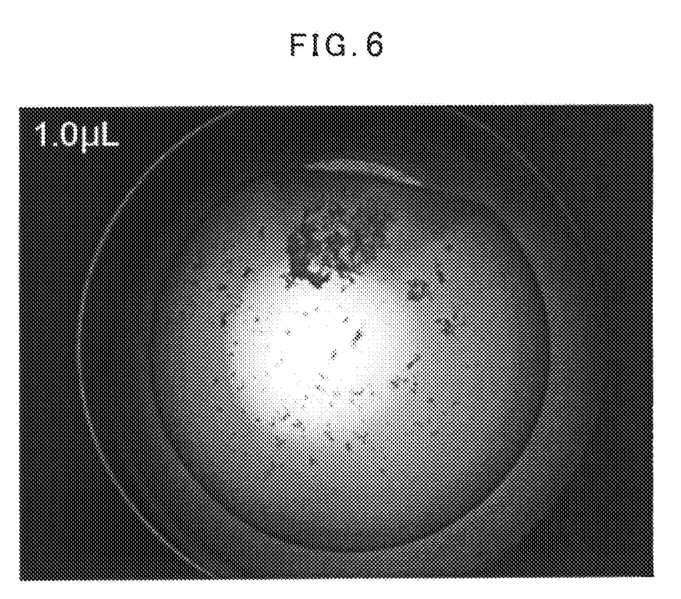
FIG. 6 is a photomicrograph of a fiber-containing crystal obtained in Example 3.
Figure 7:
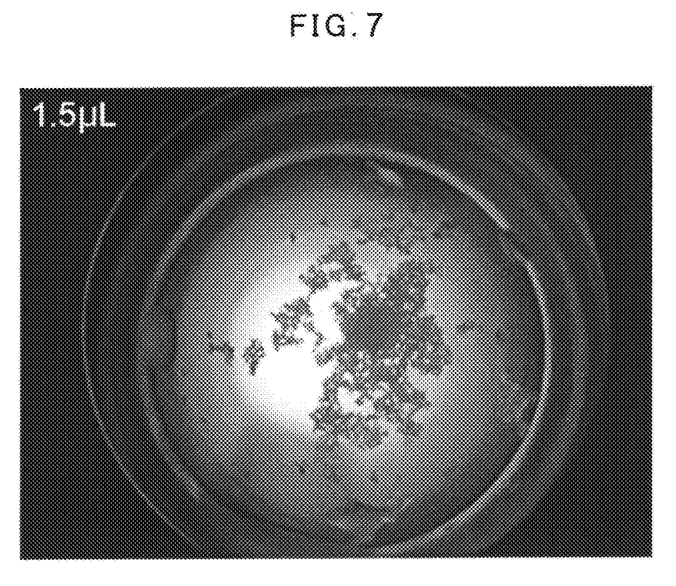
FIG. 7 is a photomicrograph of a fiber-containing crystal obtained in Example 4.
Figure 8:
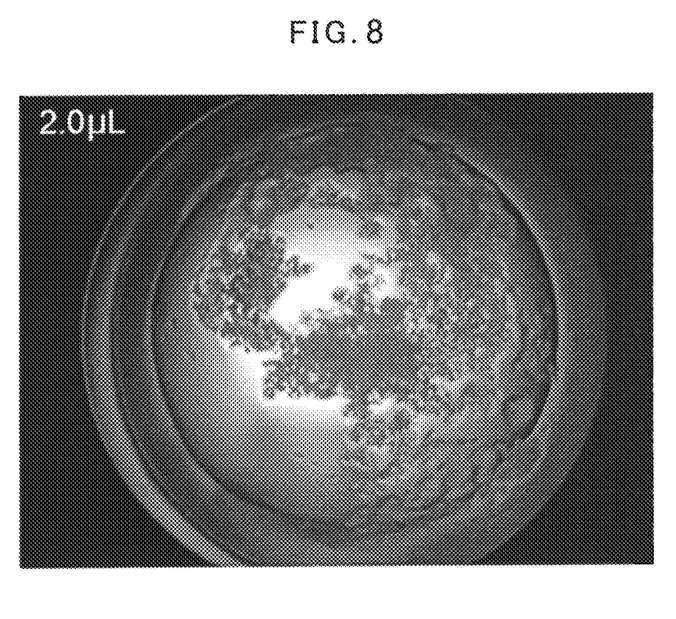
FIG. 8 is a photomicrograph of a fiber-containing crystal obtained in Example 5.

More specifically, a diffraction image of the fiber-containing crystal can be appropriately analyzed as shown in FIGS. 2 and 4. FIG. 2 is a diffraction image of a fiber-containing crystal (a crystal in which a crystal body of lysozyme incorporates fibers contained in the supernatant, which are obtained by centrifugal separation of aramid pulp fiber) immersed in the anti-freeze agent (an aqueous solution of 0.2 M sodium acetate-5% NaCl-25% glycerol) for 120 seconds in the freezing step. FIG. 3 is a diffraction image of a conventional crystal (a lysozyme crystal) which does not contain fibers immersed in the anti-freeze agent (an aqueous solution of 0.2 M sodium acetate-5% NaCl-25% glycerol) for 120 seconds in the freezing step. As shown in FIG. 2, even though the fiber-containing crystal prepared is immersed in the anti-freeze agent for 120 seconds, the crystal does not disintegrate, and a good diffraction image can be obtained. On the other hand, when the conventional crystal is immersed in the anti-freeze agent for 120 seconds, the crystal disintegrates, and an analyzable diffraction image cannot be obtained as shown in FIG. 3.

Also, FIG. 4 shows a diffraction image of the fiber-containing crystal (a crystal in which aramid pulp fiber is incorporated in a crystal body of lysozyme) immersed in the anti-freeze agent (an aqueous solution of 0.2 M sodium acetate-5% NaCl-25% glycerol) for 300 seconds in the freezing step. As shown in FIG. 4, even though the fiber-containing crystal prepared is immersed in the anti-freeze agent for a long period of time, the crystal structure does not disintegrate, and a good diffraction image can be obtained. As described above, even though the fiber-containing crystal is immersed in the anti-freeze agent over a long period of time such as 120 seconds or 300 seconds, the crystal does not disintegrate, and a good diffraction image can be obtained. Therefore, unlike the conventional crystal, which can endure only short-time immersion (such as 10 seconds), the method of preparing the fiber-containing crystal allows a sufficient operation time, and the anti-freeze agent can be sufficiently applied to the fiber-containing crystal.

Apparatus for Preparing Fiber-Containing Crystal

An apparatus for preparing the fiber-containing crystal comprises a fiber holding part on which a plurality of fibers are laid; a solution holding part holding a solution in which a biological substance or the like is dissolved; a solution addition part extracting the solution from the solution holding part and adding the solution onto the plurality of fibers laid on the fiber holding part; and an extraction part extracting, out of the crystals precipitated in the solution after a predetermined period of time, a fiber-containing crystal incorporating at least a part of the plurality of fibers inside. The below describes constitutions thereof respectively.

Fiber Holding Part

The fiber holding part is a part on which a plurality of fibers are laid. For example, the fiber holding part is a plate on which a plurality of dried fibers are laid. The shape of the plate is not particularly limited. The plate is preferably a flat, bottomed cylindrical plate (e.g., a petri dish) because that allows easy addition of a solution thereto by a solution addition part as described below.

As the fiber to be laid on the fiber holding part, the above-mentioned fiber is preferably used. In particular, fibers obtained by dispersing beaten fibers in a solvent and applying or dropping the supernatant obtained by centrifugal separation of the yielded solution are preferably used. The applying or dropping of the supernatant described above may be performed not only once but multiple times.

Solution Holding Part

The solution holding part is a part holding a solution in which the biological substance or the like is dissolved. For example, the solution holding part is a container storing a solution in which the biological substance or the like is dissolved. The shape of the container is not particularly limited. The container is preferably a wide-mouth container having an opening on the upper surface (e.g., a beaker) because that allows easy addition or extraction of a solution by a solution addition part as described below.

Solution Addition Part

The solution addition part is a mechanism to extract the solution from the solution holding part and adding the solution onto the plurality of fibers laid on the fiber holding part. For example, the solution addition part include a suction device (e.g., a pipette device with a suction tip attached thereto), a drive unit to drive the suction device, and a controller to control the drive unit. The controller let the drive unit drive so that the suction device sucks a predetermined amount of the solution from the solution holing part. Subsequently, the suction device is driven by the controller and the drive unit, and moved above the fiber holding part. Then the suction device is driven by the controller and the drive device to drop the solution onto the fibers.

Dropping the solution causes mixture of the plurality of fibers and the biological substance or the like in the fiber holding part. From these, as described above in the crystallization step, a fiber-containing crystal can be produced after a predetermined period of time.

Extraction Part

The extraction part is a mechanism to extract, out of the crystals precipitated in the solution after a predetermined period of time, a fiber-containing crystal incorporating at least a part of the plurality of fibers inside. For example, the extraction part includes an observation device (such as optical microscope) to observe the fiber-containing crystal and an extraction device (e.g., a pipette device with a suction tip attached thereto) to extract the fiber-containing crystal.

Extraction of the fiber-containing crystal may be performed by an observer operating these observation device and extraction device or may be automatically performed by a computer or the like executing a program in which the shape of the crystal or the like is stored in advance. The mechanical strength of the fiber-containing crystal prepared is enhanced by a plurality of fibers incorporated therein. Also, the fibers of the fiber-containing crystal are in point contact with a surface on which the crystal is precipitated (a precipitation surface). Therefore, when the extraction device is used, it can easily extract the fiber-containing crystal without directly touching the crystal body. Consequently, the crystal to be obtained is likely to be extracted without being broken. The extracted fiber-containing crystal can be appropriately subjected to the above-described freezing step and structure analysis step.

Chemical Soaking Device

A chemical soaking device mainly comprises a crystal holding part holding a fiber-containing crystal; a chemical holding part holding a chemical solution in which a chemical is dissolved; and a chemical addition part extracting the chemical from the chemical holding part and adding the chemical to the fiber-containing crystal. The below describes constitutions thereof respectively.

Crystal Holding Part

The crystal holding part is a part holding a fiber-containing crystal. The crystal holding part may be the fiber holding part described in the above apparatus for preparing the fiber-containing crystal or may be a different part on which the fiber-containing crystal extracted by the above-described method of preparing the fiber-containing crystal or apparatus for preparing the fiber-containing crystal is placed. When the fiber holding part also serves as a crystal holding part, the apparatus for preparing the fiber-containing crystal and the chemical soaking device can be integrated as a series of devices. On the other hand, when the crystal holding part is a distinct part, the influence of excess fibers remaining in the crystal holding part can be excluded. When the crystal holding part is a distinct part, it is, for example, a separately prepared plate. The plate is preferably a plate having a plurality of wells (recesses) formed thereon. Each well can store the fiber-containing crystal.

Chemical Holding Part

The chemical holding part is a part holding chemical solutions in which chemical agents are dissolved. For example, the chemical holding part is a plate having a plurality of wells (recesses) formed thereon, wherein chemical solutions in which chemical agents are dissolved are stored in the wells. In each well, each of a plurality of chemical agents of different types and concentrations can be stored.

Chemical Addition Part

The chemical addition part is a mechanism of extracting a chemical agent from the chemical holding part and adding the chemical agent to the fiber-containing crystal. For example, the chemical addition part includes a suction device (e.g., a pipette device with a suction tip attached thereto), a drive unit to drive the suction device, and a controller to control the drive unit. The controller let the drive unit drive so that the suction device sucks a predetermined amount of a chemical agent from a predetermined well of the chemical holding part. Subsequently, the suction device is driven by the controller and the drive unit, and moved above the crystal holding part. Then the suction device is driven by the controller and the drive device to drop the chemical onto the fiber-containing crystal.

The chemical addition part repeats the above operation multiple times so that it can add a plurality of chemical agents of different types and concentrations to the fiber-containing crystals contained in the respective wells. Further, for example, the suction device may be redesigned to be able to handle multiple chemicals simultaneously so that it can add a plurality of chemical agents of different types and concentrations to the respective fiber-containing crystals contained in a plurality of wells at once.

The chemical is dropped to be mixed with the fiber-containing crystal in the crystal holding part. From these, as described above in the crystallization step, a complex of the biological substance or the like and the chemical can be produced after a predetermined period of time. The produced complex is extracted as a complex crystal appropriately by the extraction part described above, then, appropriately subjected to the above-described freezing step and structure analysis step.

A chemical that can exhibit activity against the fiber-containing crystal can be easily searched for. This remarkably improves the convenience of the chemical soaking. In particular, when a plurality of chemicals are added to a plurality of fiber-containing crystals by a single operation, a chemical which can exhibit activity can be easily and quickly searched for.

In the above, one example is described. This disclosure is not particularly limited to the above example. The above example mainly describes the following:

(1) A fiber-containing crystal comprising a crystal body which is a crystal of a biological substance and a plurality of fibers at least partially incorporated in the crystal body.

According to this constitution, a fiber-containing crystal comprises a crystal body and a plurality of fibers partially incorporated in the crystal body. Even if the crystal body comprises a biological substance which tends to form a brittle crystal, the mechanical strength of the fiber-containing crystal to be obtained is enhanced by the plurality of fibers incorporated therein. Also, the fibers of such fiber-containing crystal can be in point contact with a surface on which the crystal is precipitated (a precipitation surface). Therefore, when, for example, a cryoloop is used to extract the crystal by scooping it up, the crystal can be easily extracted from the precipitation surface, compared with the case where the crystal body itself is in surface contact with the precipitation surface. Consequently, the fiber-containing crystal to be obtained is likely to be extracted without being broken. Also, the plurality of fibers can be incorporated in the crystal body in irregular directions respectively. Therefore, these fibers are, for example, in crystal structure analysis, less likely to be recognized as a diffraction point and hardly affect a structure analysis result. Consequently, highly accurate structure analysis of the fiber-containing crystal is possible. Even if they are in order and generate a diffraction point, structure analysis can be performed by measuring a diffraction point with only ordered fibers and removing it from a diffraction result of the fiber-containing crystal.

(2) A fiber-containing crystal comprising a crystal body which is an easy-disintegrating crystal and a plurality of fibers which are at least partially incorporated in the crystal body.

According to this constitution, a fiber-containing crystal comprises a crystal body and a plurality of fibers partially incorporated in the crystal body. Thus, even if the crystal is an easy-disintegrating crystal, the mechanical strength of the fiber-containing crystal to be obtained is enhanced by the plurality of fibers incorporated therein. Also, the fibers of such fiber-containing crystal can be in point contact with a surface on which the crystal is precipitated (a precipitation surface). Therefore, when, for example, a cryoloop is used to extract the crystal by scooping it up, the crystal can be easily extracted from the precipitation surface, compared to when the crystal body itself is in surface contact with the precipitation surface. Consequently, the fiber-containing crystal to be obtained is likely to be extracted without being broken. Also, the plurality of fibers can be incorporated in the crystal body in irregular directions respectively. Therefore, these fibers are, for example, in crystal structure analysis, less likely to be recognized as a diffraction point and hardly affect a structure analysis result. Consequently, highly accurate structure analysis of the fiber-containing crystal is possible. Even if they are in order and generate a diffraction point, structure analysis can be performed by measuring a diffraction point with only ordered fibers and removing it from a diffraction result of the fiber-containing crystal.

(3) The fiber-containing crystal according to (1) or (2), wherein the biological substance is a biopolymer, a protein, a peptide, a nucleic acid, or a sugar chain.

According to this constitution, the structure of these biological substances can be analyzed with high accuracy. This can improve the convenience in developing drugs and the like that can act on these biological substances.

(4) The fiber-containing crystal according to (3), wherein the biological substance is selected from a natural protein, a synthetic protein, an artificial protein, a natural peptide, a synthetic peptide, an artificial peptide, a natural nucleic acid, a synthetic nucleic acid, an artificial nucleic acid, a natural sugar chain, a synthetic sugar chain, and an artificial sugar chain.

According to this constitution, the structure of these biological substances can be analyzed with high accuracy. This can improve the convenience in developing drugs and the like that can act on these biological substances.

(5) The fiber-containing crystal according to any one of (1) to (4), wherein the fiber has a thickness of 1 nm to 0.1 mm.

According to this constitution, a fiber of such size is likely to be incorporated partially in the crystal body. Thus, the crystal to be obtained is easier to handle, and highly accurate structure analysis thereof is easier to perform.

(6) The fiber-containing crystal according to any one of (1) to (5), wherein the fiber is an aramid fiber, a cellulose fiber, or a polyarylate fiber.

According to this constitution, fine processing of the fiber is easy. Also, the fiber is likely to be incorporated in the crystal body. Further, the fiber is excellent in mechanical properties such as strength and elasticity. In addition, the fiber in the fiber-containing crystal to be obtained hardly affects a structure analysis result.

(7) The fiber-containing crystal according to any one of (1) to (6), which is for structure analysis.

According to this constitution, the fiber-containing crystal to be obtained has an enhanced mechanical strength compared to that of conventional crystals and is easy to handle. Therefore, the fiber-containing crystal is particularly useful for structure analysis.

(8) The fiber-containing crystal according to (7), wherein the structure analysis is x-ray crystal structure analysis, neutron crystal structure analysis, or electron microscope observation.

According to this constitution, the fiber-containing crystal to be obtained, which has sufficient mechanical strength, is less likely to be broken and can maintain its crystal quality even in those structure analyses. Therefore, highly reliable analysis data is likely to be obtained.

(9) A method of preparing a fiber-containing crystal, comprising a preparation step of preparing a plurality of fibers; an addition step of adding a solution in which a biological substance is dissolved to the plurality of fibers; a crystallization step of precipitating a crystal by increasing the concentration of the biological substance in the solution; and an extraction step of extracting, out of the obtained crystals, a fiber-containing crystal incorporating at least a part of a plurality of fibers inside.

According to this constitution, in the preparation step, a plurality of fibers are prepared. Thus, a problem such as drying of gel does not occur unlike, for example, the conventional way using gel. Also, the addition step is simple, where it is only necessary to add a solution in which a biological substance is dissolved onto the fibers. Also, in the extraction step, the crystal is hardly broken and easily extracted.

(10) The method of preparing the fiber-containing crystal according to (9), further comprising a chemical immersion step of immersing the fiber-containing crystal, which is extracted, in a chemical solution in which a chemical is dissolved.

According to this constitution, a chemical which can exhibit activity against the obtained crystal can be easily searched for. This remarkably improves the convenience of the chemical soaking.

(11) The method of preparing the fiber-containing crystal according to (9), further comprising a freezing step of freezing the fiber-containing crystal after the extraction step.

According to this constitution, the obtained crystal can be appropriately frozen. The crystal contains a plurality of fibers. When such crystal is frozen, the crystal structure thereof is less likely to be broken. That makes various kinds of structure analysis such as x-ray crystal structure analysis more applicable to the frozen crystal.

(12) The method of preparing the fiber-containing crystal according to (10), further comprising a freezing step of freezing the fiber-containing crystal after the chemical immersion step.

According to this constitution, the obtained crystal is combined with a chemical and can be appropriately frozen. The crystal contains a plurality of fibers. When a complex crystal such as this is frozen, the crystal structure thereof is less likely to be broken. That makes various kinds of structure analysis such as x-ray crystal structure analysis more applicable to the frozen complex crystal. Consequently, the manner of the bonding between the biological substance in the fiber-containing crystal and the chemical can be easily analyzed.

(13) The method of preparing a crystal according to (11) or (12), wherein the freezing step is a step of freezing the fiber-containing crystal after the fiber-containing crystal is immersed in an anti-freeze agent.

According to this constitution, water in the fiber-containing crystal is frozen in an amorphous state. Consequently, the moisture in the fiber-containing crystal hardly affects a structure analysis result.

(14) An apparatus for preparing the fiber-containing crystal, comprising a fiber holding part on which a plurality of fibers are laid; a solution holding part holding a solution in which a biological substance is dissolved; a solution addition part extracting the solution from the solution holding part and adding the solution onto the plurality of fibers laid on the fiber holding part; and an extraction part extracting, out of the crystals precipitated in the solution after a predetermined period of time, a fiber-containing crystal incorporating at least a part of the plurality of fibers inside.

According to this constitution, a fiber-containing crystal incorporating a plurality of fibers is prepared. The mechanical strength of the crystals to be obtained is enhanced by a plurality of fibers incorporated therein. Also, the fibers of the fiber-containing crystal can be in point contact with a surface on which the crystal is precipitated (a precipitation surface). Consequently, compared to when the crystal itself is in surface contact with the precipitation surface, it is easy to extract from the deposition surface. Therefore, the crystal can be easily extracted from the precipitation surface, compared to when the crystal body itself is in surface contact with the precipitation surface. Consequently, the obtained crystal is easily extracted without being broken. The plurality of fibers can be incorporated in the crystal body in irregular directions respectively. Therefore, these fibers are, for example, in crystal structure analysis, less likely to be recognized as a diffraction point and hardly affect a structure analysis result. Consequently, highly accurate structure analysis of the fiber-containing crystal is possible.

(15) A chemical soaking device, comprising a crystal holding part holding a fiber-containing crystal, wherein the fiber-containing crystal contains a crystal body which is a crystal of a biological substance and a plurality of fibers at least partially incorporated in the crystal body; a chemical holding part holding a chemical solution in which a chemical is dissolved; and a chemical addition part extracting the chemical from the chemical holding part and adding the chemical to the fiber-containing crystal.

According to this constitution, a chemical is added to a fiber-containing crystal incorporating a part of a plurality of fibers. Thus, a chemical which can exhibit activity against the obtained crystal can be easily searched for. This can remarkably improve the convenience of the chemical soaking.

(16) The chemical soaking device according to (15), wherein the chemical comprise different types of chemical agents; the crystal holding part is provided with a plurality of wells, each of which stores the fiber-containing crystal; and the chemical addition part drops each of the different types of chemical agents to the fiber-containing crystal stored in each of the wells.

According to this constitution, activities of a plurality of chemical agents against a crystal can be examined by a single operation. Thus, a chemical which can exhibit activity against the crystal can be easily and quickly searched for. This can remarkably improve the convenience of the chemical soaking.

EXAMPLE

Our crystals, methods and apparatus are described below in more detail in reference to examples. This disclosure is not limited to these examples.

Calculation Method of Characteristic Values

Fiber Diameter

With fibers observed by an 80 times magnification stereomicroscope, 10 (±1) pieces of fibers which were as clearly observable as their measurement were possible were randomly extracted, their fiber diameters were measured, and the arithmetic mean value of the diameters was obtained for obtaining the fiber diameter.

Example 1, Comparative Example 1

Preparation of Fiber-Containing Crystal

Preparation Step

First, pulp-like meta-aramid fiber was dried, 0.02 g of the dried fiber was suspended in 1 mL of ethanol, and centrifugal separation thereof was performed under the condition of 1800 rpm and 10 seconds, and the resultant supernatant was collected. A plate provided with a well having a depth of 4 mm and a diameter of 8 mm (also referred to as a protein well for containing a protein solution) and a well having a depth of 16 mm and a diameter of 17 mm (also referred to as a reservoir well for containing a reservoir solution) was prepared, and 200 µL of a prepared reservoir solution (0.2 M sodium acetate buffer (pH 4.5)-5% NaCl) was placed in the reservoir well. Then 2 µL of the resultant supernatant was dropped to the plate bottom of the protein well and dried so that the fiber was laid in the protein well. It was found that the laid, dried fiber (meta-aramid pulp) had a thickness (diameter) of approximately 2 µm and a weight of approximately 1.2 mg. For comparison, a reservoir solution was placed in a well having no fibers laid, and the same operation was performed.

Addition Step

1 µl of a solution (0.2 M sodium acetate buffer, concentration: 20 mg/mL) in which a biological substance (lysozyme) was dissolved was added onto the fiber in the protein well, 1 μl of a reservoir solution was added thereto, and subsequently the fiber and the solution were appropriately mixed.

Crystallization Step

The protein well, to which the above biological substance had been added, and the reservoir well were sealed with a tape and left to stand in an incubator at 20° C. for 24 hours or more. From an observation using an 80 times magnification stereomicroscope, it was confirmed that about two to three crystals having a size of approximately 200 μm were produced. FIG. 1 was a photomicrograph of that fiber-containing crystal. The observation showed tendencies that crystals were likely to be precipitated at portions where the fibers were present and a crystal which incorporates a lot of fibers was likely to be produced if there were a large number of fibers present.

Extraction Step

Out of the produced crystals, only a fiber-containing crystal was extracted with a cryoloop (radius: 0.2 to 0.4 mm).

Structure Analysis Step

Next, the fiber-containing crystal was scooped up together with the fibers surrounding the crystal with a cryoloop (radius: 0.2 to 0.4 mm) and mounted to an x-ray crystal structure analyzer manufactured by Rigaku Corporation, Micro Max, (where the x-ray source was a Cu-Kα and the imaging plate detector was R-AXIS VII). The fiber-containing crystal was immersed for 10 seconds in a cryoprotectant solution which had been adjusted to have the final concentration of an aqueous solution of 0.2 M sodium acetate-5% NaCl-25% glycerol prior to analysis, and subsequently, it was instantaneously frozen at −196° C. using liquid nitrogen (freezing step). Thereafter, x-ray diffraction measurement of the frozen crystal was performed under the conditions of an exposure time of 15 seconds, a distance of 85 mm, and a vibration angle of 0.5 to 1.0° in a low-temperature environment (−173° C.), and that provided a good diffraction image. Also, the result of the structure analysis using the diffraction image confirmed that, even if the fiber had been included, the same protein structure as that of the conventional method was obtained. The evaluation of the diffraction image was performed by using HLK 2000 (available from Rigaku Corporation). Also, the evaluation of the diffraction point was performed on the basis that the resolution was lower than 2 angstroms and the spot was clear.

In addition, irradiations of x-rays were performed in different immersion time conditions in the cryoprotectant solution. Specifically, the immersion time in the cryoproteinase solution was changed to 120 seconds and 300 seconds for comparison of crystal strengths. FIG. 2 is a diffraction image of a fiber-containing crystal which was immersed in an anti-freeze agent for 120 seconds in the freezing step. FIG. 4 is a diffraction image of a fiber-containing crystal which was immersed in an anti-freeze agent for 300 seconds in the freezing step. In the evaluation of the crystal formed without laying fibers being laid, when the immersion time was 120 seconds, no diffraction point was observed. FIG. 3 is a diffraction image of a crystal of Comparative Example 1 which was immersed in the anti-freeze agent for 120 seconds in the freezing step. Further, it was found that, in a crystal formed with fibers being laid, a diffraction point appeared even if the immersion time was 900 seconds or longer.

Comparative Examples 2 to 5

Fiber-containing crystals were prepared in the same way as Example 1, except that the dropping amount of the supernatant containing the fibers obtained in Example 1 into the well was changed to 0.5 μL (in Example 2), 1.0 μL (Example 3), 1.5 μL (Example 4), and 2.0 μL (Example 5). For crystallization, the well was left to stand in an incubator at 20° C. for 1 to 3 days until an approximately 0.2 mm crystal was obtained. The results are shown in FIG. 5 to FIG. 8. FIG. 5 to FIG. 8 are photomicrographs of the fiber-containing crystals obtained in Examples 2 to 5, respectively.

With the obtained crystal, the following soaking test was performed. For the soaking test, a 40% aqueous solution of 0.2 M sodium acetate-5% NaCl-dimethyl sulfoxide (DMSO) was used. Each crystal formed in the well was scooped with a cryoloop and immersed in the 40% aqueous solution of 0.2 M sodium acetate-5% NaCl-DMSO. Observations on those crystals were performed by using an 80 times magnification stereomicroscope to measure lengths of time until they showed appearance collapse, and thus they were compared in strength. The results were shown in FIG. 11. What the "appearance collapse" in the evaluation means is that, different from the disintegration caused when the crystal was immersed in the anti-freeze agent, a change occurs in the appearance of the crystal.

Figure 11:
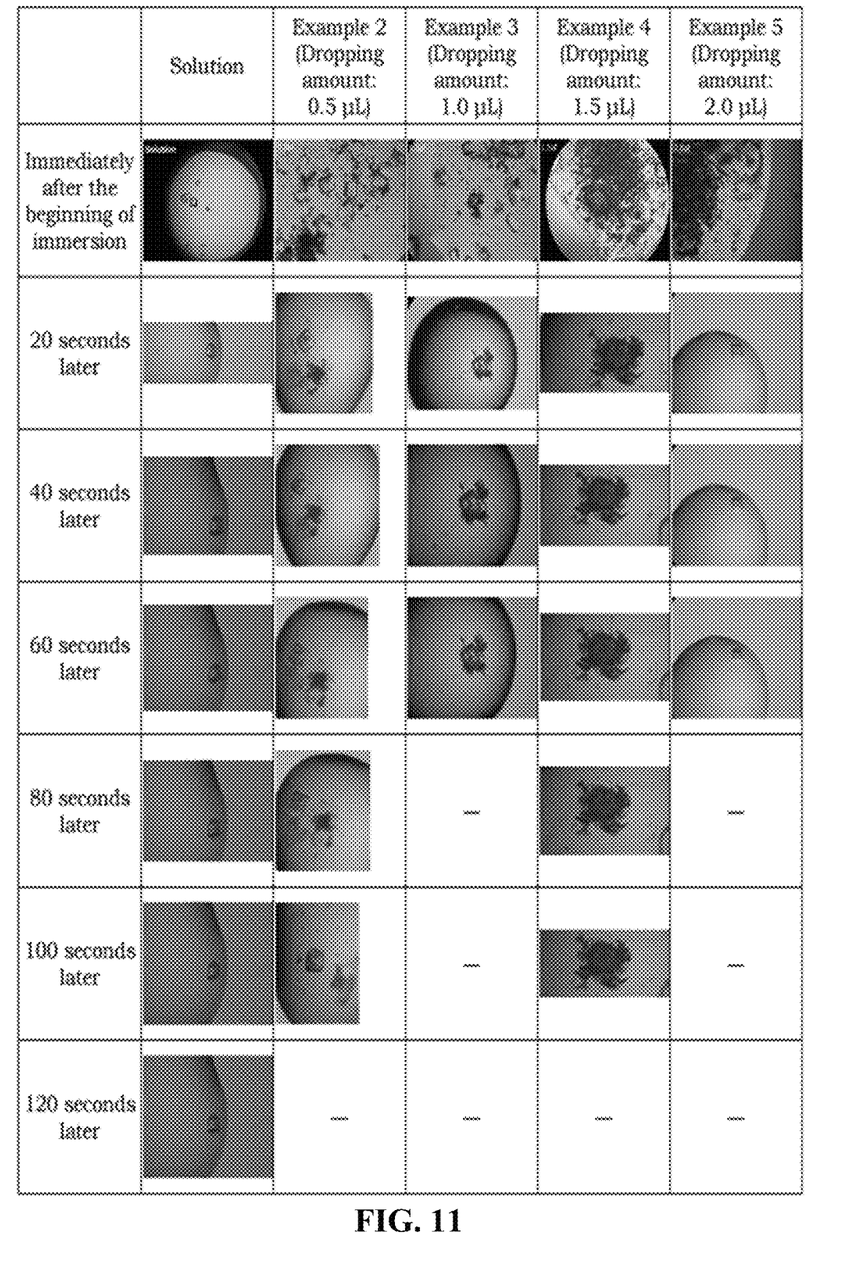
FIG. 11 is a table showing the appearance of crystals obtained in Examples 2-5 in response to a soaking test.

As shown in FIG. 11, a Solution crystal which contains no fibers showed appearance collapse after 20 seconds, and, in contrast, many of the crystals which were crystallized with fibers so that the fibers were incorporated therein showed appearance collapse after about 40 seconds. Further, among them, the one which incorporated far more fibers than the others (Example 4 in FIG. 11) took 100 seconds, longer than 40 seconds, to show appearance collapse. In Example 5, appearance collapse was observed after 40 seconds. However, this might be because the crystallization had occurred at a portion where there had been few fibers to be observed. Even so, the strength of the crystal was improved compared to that of a crystal which had not been formed without fibers being laid (e.g., a Solution crystal).

Examples 6, 7, Comparative Example 2, Reference Example 1, Reference Comparative Example 1

Crystals having different amounts of fibers had been obtained even on plates having the same amount of fibers laid thereon, and thus soaking tests of those were also performed in the similar manner. Specifically, fiber-containing crystals formed on the wells were observed with an 80 times magnification stereomicroscope so that, among those, a fiber-containing crystal containing a relatively large number of fibers (Example 6) and a fiber-containing crystal in which no fibers were observed (Example 7) were extracted, and soaking tests were performed in the same manner as Example 2. In addition, as Comparative Example 2, the crystals obtained in Comparative Example 1, which contained no fibers, was extracted and subjected to a soaking test. The results show that the lengths of time until the crystal showed appearance collapse were 100 seconds (in Example 6), 40 seconds (in Example 7), and 20 seconds (in Comparative Example 2), respectively.

Thus, we inferred that the fiber-containing crystal containing many fibers which could be observed with an 80 times magnification stereomicroscope has better soaking resistance and enhanced strength. However, comparison between the crystal of Comparative Example 1, which contained no fibers at all, and the crystal of Example 7, which was formed on the fibers laid, but had no observable fibers in the observation using an 80 times magnification stereomicroscope showed that the latter took longer time until crystal appearance collapse. Therefore, we inferred that fine fibers not observable with an 80 times magnification stereoscopic observation were present, and that enhanced the strength of the crystal.

Figure 9:
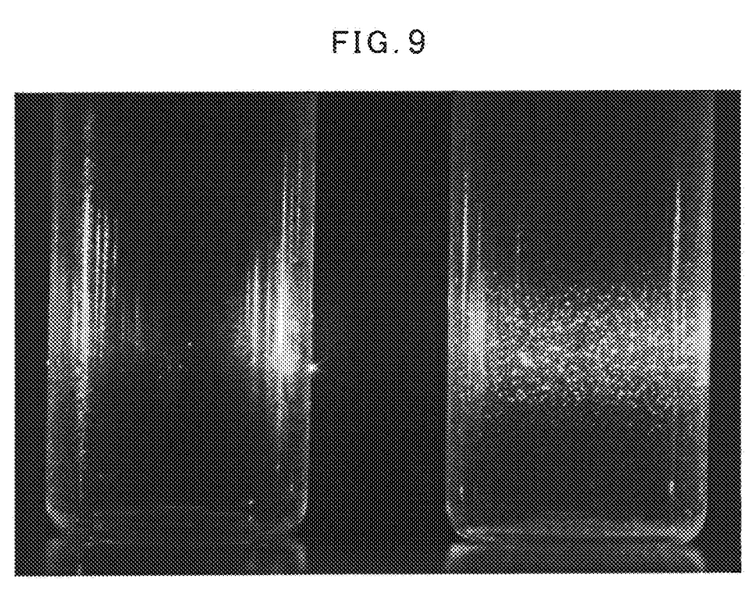
FIG. 9 is a photograph of the appearances of the supernatants of Reference Example 1 and Reference Comparative Example 1.

The presence of the above fine fibers was examined by the following method: 1 mL of a supernatant obtained by the same method as described in Example 1 was further subjected to a centrifugal separation at 1800 rpm for 10 seconds, and, after relatively thick fibers were sunk, the resultant supernatant was collected (Reference Example 1). The presence of fibers in this supernatant could not be confirmed with the unaided eyes. This supernatant was placed in a 1 mL vial bottle, a laser having a wavelength of 532 nm was irradiated thereto, and the particle size was obtained by Rayleigh scattering and Mie scattering. As a result, particle sizes of approximately 50 nm and approximately 500 nm were be confirmed. As Reference Comparative Example 1, a similar vial bottle was prepared, except that the supernatant liquid was changed to ethanol, and the laser was irradiated on it. As a result, no luminescent spot was confirmed. The results are shown in FIG. 9. The photographing conditions, with a single-lens reflex camera (manufactured by Nikon Corporation), were as follows: the shutter speed was 1/10, the aperture value (f-stop) was 20, and the exposure compensation was −5. FIG. 9 is a photograph of the appearances of the supernatants of Reference Example 1 and Reference Comparative Example 1. The left is the supernatant of the Reference Comparative Example 1 and the right is the supernatant of Reference Example 1. For FIG. 9, the following image processing was performed. First, the image photographed by View NX was converted to JPEG, and then, EasyAccess was used to obtain the luminance information. The average values of the numbers of luminescent spots in Rayleigh scattering and Mie scattering are shown below. The numbers of luminescent spots were counted in a range of 200×180 pixels.
Rayleigh Scattering
Comparative Reference Example 1: 5.5
Reference Example 1: 52
Mie Scattering
Comparative Reference Example 1: 1.2
Reference Example 1: 21.8

The presence of fibers was confirmed in the supernatant of Reference Example 1, and it is thus considered that, in the supernatant of Example 1, fine fibers which were not observable with the unaided eyes were suspended. Therefore, it is considered that the reason why the crystals formed in a portion where there was no fibers observable with a stereomicroscope had better soaking resistance than that of the crystal formed without fibers being laid is that the former had incorporated the fine fibers while growing.

Example 8

Figure 10:
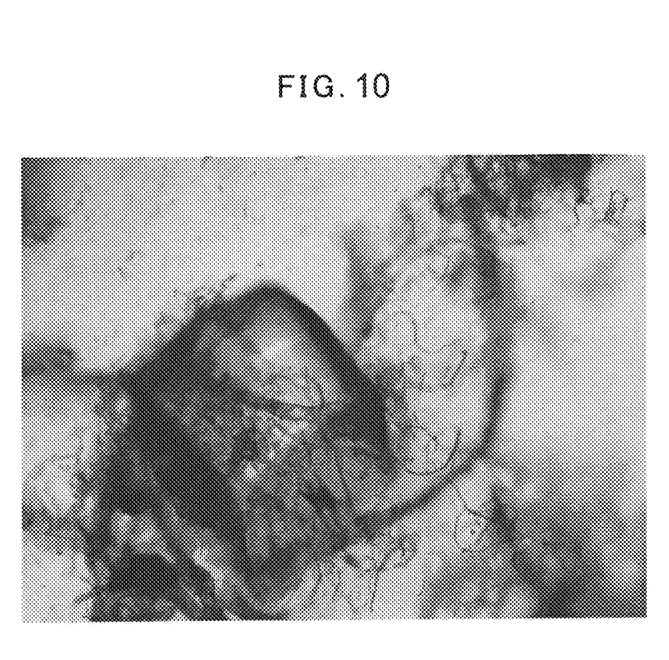
FIG. 10 is a photomicrograph of a fiber-containing crystal obtained in Example 8.

Crystallization was performed in the same manner as in Example 1, except that a pulp-like para-aramid fiber (Kevlar (registered trademark) pulp, manufactured by Du Pont-Toray Co., Ltd.) was used instead of a pulp-like meta-aramid fiber. FIG. 10 is a photomicrograph of the fiber-containing crystal of Example 8. As shown in FIG. 10, even when the pulp-like para-aramid fiber was used, the fiber-containing crystal was obtained as in Example 1.

The invention claimed is:

1. A fiber-containing crystal comprising a crystal body which is a crystal of a biological substance and a plurality of fibers at least partially incorporated in the crystal body,
    wherein the fiber is a polyolefin-based fiber selected from the group consisting of polyethylene, a nylon-based fiber, a polyester-based fiber, an acryl-based fiber, an aramid fiber, a cellulose-based fiber and a polyarylate fiber.

2. A fiber-containing crystal comprising a crystal body which is an easy-disintegrating crystal and a plurality of fibers at least partially incorporated in the crystal body,
    wherein the fiber is a polyolefin-based fiber selected from the group consisting of polyethylene, a nylon-based fiber, a polyester-based fiber, an acryl-based fiber, an aramid fiber, a cellulose-based fiber and a polyarylate fiber.

3. The fiber-containing crystal according to claim 1, wherein the biological substance is a biopolymer, a protein, a peptide, a nucleic acid, or a sugar chain.

4. The fiber-containing crystal according to claim 3, wherein the biological substance is selected from a natural protein, a synthetic protein, an artificial protein, a natural peptide, a synthetic peptide, an artificial peptide, a natural nucleic acid, a synthetic nucleic acid, an artificial nucleic acid, a natural sugar chain, a synthetic sugar chain, and an artificial sugar chain.

5. The fiber-containing crystal according to claim 1, wherein the fiber has a thickness of 1 nm to 0.1 mm.

6. The fiber-containing crystal according to claim 1, which is for structural analysis.

7. The fiber-containing crystal according to claim 6, wherein the structure analysis is x-ray crystal structure analysis, neutron crystal structure analysis, or electron microscope observation.

8. A method of preparing a fiber-containing crystal, comprising:
    a preparation step of preparing a plurality of fibers;
    an addition step of adding a solution in which a biological substance is dissolved to the plurality of fibers;
    a crystallization step of precipitating a crystal by increasing the concentration of the biological substance in the solution; and
    an extraction step of extracting, out of the obtained crystals, a fiber-containing crystal incorporating at least a part of a plurality of fibers inside,
    wherein the fiber is a polyolefin-based fiber selected from the group consisting of polyethylene, a nylon-based fiber, a polyester-based fiber, an acryl-based fiber, an aramid fiber, a cellulose-based fiber and a polyarylate fiber.

9. The method according to claim 8, further comprising a chemical immersion step for immersing the fiber-containing crystal, which is extracted, in a chemical solution in which a chemical is dissolved.

10. The method according to claim 8, further comprising a freezing step of freezing the fiber-containing crystal after the extraction step.

11. The method according to claim 9, further comprising a freezing step of freezing the fiber-containing crystal after the chemical immersion step.

12. The method according to claim 10, wherein the freezing step is a step of freezing the fiber-containing crystal after the fiber-containing crystal is immersed in an anti-freeze agent.

* * * * *